(12) United States Patent
Valadez

(10) Patent No.: US 9,218,656 B2
(45) Date of Patent: Dec. 22, 2015

(54) METHOD AND SYSTEM FOR AUTOMATIC CLASSIFICATION OF LESIONS IN BREAST MRI

(75) Inventor: Gerardo Hermosillo Valadez, West Chester, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1257 days.

(21) Appl. No.: 12/244,049

(22) Filed: Oct. 2, 2008

(65) Prior Publication Data

US 2009/0093711 A1 Apr. 9, 2009

Related U.S. Application Data

(60) Provisional application No. 60/977,752, filed on Oct. 5, 2007.

(51) Int. Cl.
| | |
|---|---|
| *A61B 5/055* | (2006.01) |
| *G06K 9/00* | (2006.01) |
| *G06T 7/00* | (2006.01) |
| *A61B 5/00* | (2006.01) |
| *G06F 19/00* | (2011.01) |

(52) U.S. Cl.
CPC ............. *G06T 7/0012* (2013.01); *A61B 5/055* (2013.01); *A61B 5/7264* (2013.01); *G06F 19/321* (2013.01); *G06F 19/345* (2013.01); *A61B 5/7267* (2013.01); *G06F 19/3468* (2013.01); *G06T 2207/10088* (2013.01); *G06T 2207/30068* (2013.01)

(58) Field of Classification Search
CPC .............. G06F 19/3468; G06F 19/321; G06F 19/3456; G06T 2207/30068; G06T 2207/10088
USPC .......... 600/407, 420, 300, 410; 382/128, 130, 382/224
See application file for complete search history.

(56) References Cited

U.S. PATENT DOCUMENTS

| | | | |
|---|---|---|---|
| 2002/0029120 A1* | 3/2002 | Degani .......................... | 702/100 |
| 2004/0064037 A1* | 4/2004 | Smith .......................... | 600/420 |
| 2005/0113651 A1* | 5/2005 | Wood et al. .................... | 600/300 |
| 2006/0110018 A1* | 5/2006 | Chen et al. .................... | 382/130 |
| 2007/0133852 A1* | 6/2007 | Collins et al. ................. | 382/128 |
| 2008/0125643 A1* | 5/2008 | Huisman et al. .............. | 600/420 |

OTHER PUBLICATIONS

Gibbs, et al., "Textural analysis of contrast-enhanced MR images of the breast", Magnetic Resonance in Medicine, vol. 50, No. 1, Jun. 13, 2003, pp. 92-98.

(Continued)

*Primary Examiner* — Long V Le
*Assistant Examiner* — Katherine McDonald
(74) *Attorney, Agent, or Firm* — Peter R. Withstandley

(57) ABSTRACT

A method for classifying a lesion in an MRI includes acquiring a pre-contrast MR image. A magnetic contrast agent is administered. A set of post-contrast MR images are acquired. The acquired pre-contrast and post-contrast MR images are displayed. A manually entered value is received for a size of a lesion manually identified within the pre-contrast and post-contrast MR images. A manually entered value for an absorption/washout profile is received of the manually identified lesion. A risk of malignancy for the manually identified lesion is automatically determined based on the received size value and absorption/washout profile.

18 Claims, 4 Drawing Sheets

(56) References Cited

OTHER PUBLICATIONS

Tanner et al., "Does Registration Improve the Performance of a Computer Aided Diagnosis System for Dynamic Contrast-Enhanced MR Mammography?", Biomedical Imaging: Macro to Nano, 2006, 3rd IEEE International Symposium on Apr. 6, 2006, Piscataway, NJ, IEEE, pp. 466-496.

Liberman et al., "Does Size Matter? Positive Predictive Value of MRI-Detected Breast Lesions as a Function of Lesion Size", American Journal of Roentgenology, vol. 186, 2006, pp. 426-430.

Hermosillo et al., "Evaluation of a Computer-Aided Classification tool for Breast MR", Program and Abstract, American Roentgen Ray Society Annual Meeting, Apr. 13-18, 2008, p. 77.

International Search Report including Notification of Transmittal of the International Search Report, International Search Report, and Written Opinion of the International Searching Authority.

\* cited by examiner

METHOD AND SYSTEM FOR AUTOMATIC CLASSIFICATION OF LESIONS IN BREAST MRI

CROSS-REFERENCE TO RELATED APPLICATION

The present application is based on provisional application Ser. No. 60/977,752 filed Oct. 5, 2007, the entire contents of which are herein incorporated by reference.

BACKGROUND OF THE INVENTION

1. Technical Field

The present disclosure relates to lesion classification and, more specifically, to a method and system for automatic classification of lesions in breast MRI.

2. Discussion of Related Art

Computer aided diagnosis (CAD) is the process of using computer vision systems to analyze medical image data and make a determination as to what regions of the image data are potentially problematic. Some CAD techniques then present these regions of suspicion to a medical professional such as a radiologist for manual review, while other CAD techniques make a preliminary determination as to the nature of the region of suspicion. For example, some CAD techniques may characterize each region of suspicion as a lesion or a non-lesion. The final results of the CAD system may then be used by the medical professional to aid in rendering a final diagnosis.

Because CAD techniques may identify lesions that may have been overlooked by a medical professional working without the aid of a CAD system, and because CAD systems can quickly direct the focus of a medical professional to the regions most likely to be of diagnostic interest, CAD systems may be highly effective in increasing the accuracy of a diagnosis and decreasing the time needed to render diagnosis. Accordingly, scarce medical resources may be used to benefit a greater number of patients with high efficiency and accuracy.

CAD techniques have been applied to the field of mammography, where low-dose x-rays are used to image a patient's breast to diagnose suspicious breast lesions. However, because mammography relies on x-ray imaging, mammography may expose a patient to potentially harmful ionizing radiation. As many patients are instructed to undergo mammography on a regular basis, the administered ionizing radiation may, over time, pose a risk to the patient. Moreover, it may be difficult to use x-rays to differentiate between different forms of masses that may be present in the patient's breast. For example, it may be difficult to distinguish between calcifications and malignant lesions.

Magnetic resonance imaging (MRI) is a medical imaging technique that uses a powerful magnetic field to image the internal structure and certain functionality of the human body. MRI is particularly suited for imaging soft tissue structures and is thus highly useful in the field of oncology for the detection of lesions.

In dynamic contrast enhanced MRI (DCE-MRI), many additional details pertaining to bodily soft tissue may be observed. These details may be used to further aid in diagnosis and treatment of detected lesions.

DCE-MRI may be performed by acquiring a sequence of MR images that span a time before magnetic contrast agents are introduced into the patient's body and a time after the magnetic contrast agents are introduced. For example, a first MR image may be acquired prior to the introduction of the magnetic contrast agents, and subsequent MR images may be taken at a rate of one image per minute for a desired length of time. By imaging the body in this way, a set of images may be acquired that illustrate how the magnetic contrast agent is absorbed and washed out from various portions of the patient's body. This absorption and washout information may be used to characterize various internal structures within the body and may provide additional diagnostic information.

The absorption and washout information may thus be used to characterize a lesion as either benign or malignant. When a trained medical practitioner such as a radiologist examines image data such as DCE-MR image data, a determination may be made as to whether a suspected lesion is benign or malignant. In addition to basing this determination on the absorption and washout information, other factors may be used.

In accordance with some techniques, the determination as to whether a suspected lesion is benign or malignant is performed by the medical practitioner. In accordance with other techniques, the determination may be made by a CAD system. When the determination is made using a CAD system, the practitioner may either choose to accept the automatic decision or disregard it in favor of the practitioner's own assessment. Both options may be less than ideal. This is because, in the first case, the determination of the CAD system may be inferior to the manual determination of the practitioner, and yet, in the second case, the CAD system has not served its purpose.

SUMMARY

A method for classifying a lesion in an MRI includes acquiring a pre-contrast MR image. A magnetic contrast agent is administered. A set of post-contrast MR images are acquired. The acquired pre-contrast and post-contrast MR images are displayed. One or more manually entered factors pertaining to a lesion manually identified within the pre-contrast and post-contrast MR images are received. A risk of malignancy for the manually identified lesion is automatically determined based on the received one or more factors pertaining to the lesion.

The factors pertaining to the lesion may include a manually entered value for a size of a lesion manually identified within the pre-contrast and post-contrast MR images; and a manually entered value for an absorption/washout profile of the manually identified lesion.

The acquired pre-contrast and post contrast MR images may include a dynamic contrast enhanced MRI (DCE-MRI). The magnetic contrast agent may include a gadolinium compound.

The value for the size of the lesion and the absorption/washout profile of the lesion may be determined by a medical practitioner upon reading the displayed acquired pre-contrast and post-contrast MR images.

The risk of malignancy may be automatically determined from the received size value (s) and absorption/washout profile (t) by normalizing a value of $(s \cdot t)^3$. The risk of malignancy $R_c$ may be automatically determined from the received size value (s) and absorption/washout profile (t) according to the equation:

$$R_c(s, t) = \frac{2}{\pi}\arctan\left[\left(\frac{st}{c}\right)^3\right]$$

wherein c is a cutoff size for a progressive lesion to be considered suspicious for malignancy. The cutoff size c may be 23 millimeters. Alternatively, the cutoff size c may be determined by a training algorithm that uses a set of training data of lesions that includes characterizations of lesion sizes, absorption/washout profiles, and determinations as to whether the lesions turned out to be benign or malignant.

The absorption/washout profile (t) may be expressed as 1 when the lesion exhibits a progressive absorption, 2 when the lesion exhibits a plateau, and 3 when the lesion exhibits a washout.

A method for classifying a lesion in an MRI includes receiving a manually entered value for a size of a lesion manually identified within DCE-MR images. The lesion has been diagnosed as having an uncertain probability of malignancy. A manually entered value for an absorption/washout profile of the manually identified lesion is received. A risk of malignancy is automatically determined for the manually identified lesion based on the received size value and absorption/washout profile. The diagnosis of the lesion is recharacterized as either being benign or malignant based on the automatically determined risk of malignancy.

The DCE-MR images may be acquired along with the administration of a magnetic contrast agent including a gadolinium compound. The value for the size of the lesion and the absorption/washout profile of the lesion may be determined by a medical practitioner upon reading the DCE-MR images.

The risk of malignancy may be automatically determined from the received size value (s) and absorption/washout profile (t) by normalizing a value of $(s \cdot t)^3$. The risk of malignancy $R_c$ may be automatically determined from the received size value (s) and absorption/washout profile (t) according to the equation:

$$R_c(s, t) = \frac{2}{\pi} \arctan\left[\left(\frac{st}{c}\right)^3\right]$$

wherein c is a cutoff size for a progressive lesion to be considered suspicious for malignancy. The cutoff size c may be 23 millimeters. Alternatively, the cutoff size c may be determined by a training algorithm that uses a set of training data of lesions that includes characterizations of lesion sizes, absorption/washout profiles, and determinations as to whether the lesions turned out to be benign or malignant.

The absorption/washout profile (t) may be expressed as 1 when the lesion exhibits a progressive absorption, 2 when the lesion exhibits a plateau, and 3 when the lesion exhibits a washout.

The characterization of the lesion as having an uncertain probability of malignancy may include a classification of the lesion as a BIRADS level 3 lesion and the recharacterization of the diagnosis may include either downgrading the lesion to BIRADS level 2, upgrading the lesion to BIRADS level 4 or keeping the lesion as BIRADS level 3.

A computer system includes a processor and a program storage device readable by the computer system, embodying a program of instructions executable by the processor to perform method steps for method for classifying a lesion in an MRI. The method includes receiving a manually entered value for a size of a lesion manually identified within DCE-MR images; receiving a manually entered value for an absorption/washout profile of the manually identified lesion; and automatically determining a risk of malignancy for the manually identified lesion based on the received size value and absorption/washout profile.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
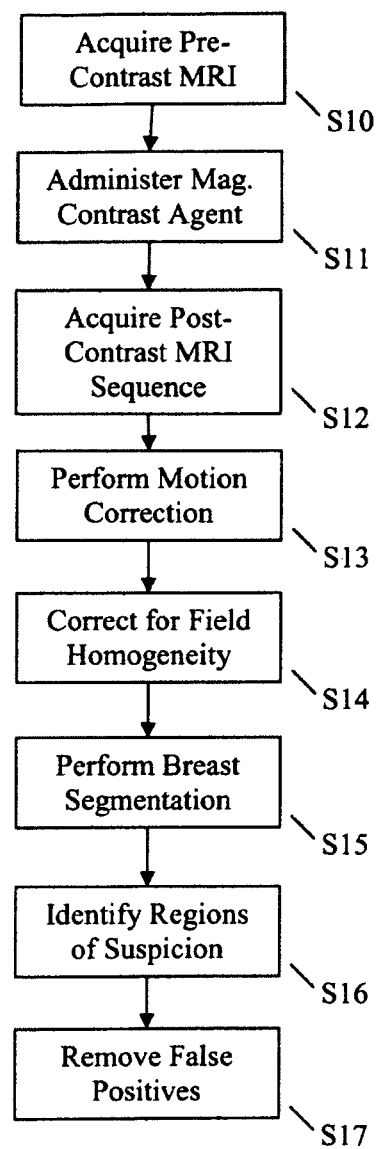
FIG. 1 is a flow chart illustrating a method for imaging a patient's breast using DCE-MRI and rendering a computer-aided diagnosis according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide a system and method for guiding a medical practitioner, such as a radiologist, in the diagnosis of one or more lesion candidates. By guiding the medical practitioner rather than providing a fully-automatic determination, exemplary embodiments of the present invention may allow for the medical practitioner to make a manual diagnosis while being assisted by a computer to help provide a consistent application of the medical practitioner's diagnostic skills and efforts. Thus, the medical practitioner may be aided in providing a consistently high level of diagnosis.

Exemplary embodiments of the present invention may permit a medical practitioner such as a radiologist and/or a radiology technician to imaging a patient's breast using DCE-MRI techniques and then identify regions of suspicion that are more likely to be malignant breast lesions. By utilizing DCE-MRI rather than mammography, additional data pertaining to contrast absorption and washout may be used to accurately distinguish between benign and malignant breast masses.

The assessment of the DCE-MR images may be performed either by the medical practitioner or by a computer-aided diagnosis (CAD) system. FIG. 1 is a flow chart illustrating a method for imaging a patient's breast using DCE-MRI and rendering a diagnosis according to an exemplary embodiment of the present invention, either with the assistance of a CAD system or manually. First, a pre-contrast MRI is acquired (Step S10). The pre-contrast MRI may include an MR image taken of the patient before the magnetic contrast agent has been administered. The pre-contrast MRI may include one or more modalities. For example, both T1 and T2 relaxation modalities may be acquired.

Next, with the patient remaining as still as possible, the magnetic contrast agent may be administered (Step S11). The magnetic contrast agent may be a paramagnetic agent, for example, a gadolinium compound. The agent may be administered orally, intravenously, or by another means. The magnetic contrast agent may be selected for its ability to appear extremely bright when imaged in the T1 modality. By injecting the magnetic contrast agent into the patient's blood, vascular tissue may be highly visible in the MRI. Because malignant tumors tend to be highly vascularized, the use of the magnetic contrast agent may be highly effective for identifying regions suspected of being lesions.

Moreover, additional information may be gleamed by analyzing the way in which a region absorbs and washes out the magnetic contrast agent. For this reason, a sequence of post-contrast MR images may be acquired (Step S12). The sequence may be acquired at regular intervals in time, for example, a new image may be acquired every minute.

As discussed above, the patient may be instructed to remain as still as possible throughout the entire image acquisition sequence. Despite these instructions, the patient will most likely move somewhat from image to image. Accordingly, before regions of suspicion are identified (Step S16), motion correction may be performed on the images (Step S13).

At each acquisition, the image may be taken in the T1 modality that is well suited for monitoring the absorption and washout of the magnetic contrast agent.

Because MR images are acquired using a powerful magnetic field, subtle inhomogeneity in the magnetic field may have an impact on the image quality and may lead to the introduction of artifacts. Additionally, the level of enhancement in the post-contrast image sequence may be affected. Also, segmentation of the breast may be impeded by the inhomogeneity, as in segmentation, it is often assumed that a particular organ appears homogeneously. Accordingly, the effects of the inhomogeneous magnetic field may be corrected for within all of the acquired MR images (Step S14).

The order in which motion correction (Step S13) and inhomogeneity correction (Step S14) are performed on the MR images is not critical. All that is required is that these steps be performed after image acquisitions for each given image, and prior to segmentation (Step S15). These corrective steps may be performed for each image after each image is acquired or for all images after all images have been acquired.

After the corrective steps (Steps S13 and S14) have been performed, breast segmentation may be performed (Step S15). Segmentation is the process of determining the contour delineating a region of interest from the remainder of the image. In making this determination, edge information and shape information may be considered.

Edge information pertains to the image intensity changes between the interior and exterior of the contour. Shape information pertains to the probable shape of the contour given the nature of the region of interest being segmented. Some techniques for segmentation such as the classical watershed transformation rely entirely on edge information. Examples of this technique may be found in L. Vincent and P. Soille, "Watersheds in digital spaces: An efficient algorithm based immersion simulations" *IEEE Trans. PAMI,* 13(6):583-589, 1991, which is incorporated by reference. Other techniques for segmentation rely entirely on shape information. For example, in M. Kass, A. Witkin, and D. Terzopoulous, "Snakes—Active contour models" *Int J. Comp Vis,* 1(4): 321-331, 1987, which is incorporated by reference, a calculated internal energy of the curvature is regarded as a shape prior although its weight is hard-coded and not learned through training. In A. Tsai, A. Yezzi, W. Wells, C. Tempany, D. Tucker, A. Fan, and W. E. Grimson, "A shape-based approach to the segmentation of medical imagery using level sets" *IEEE Trans. Medical Imaging,* 22(2): 137-154, 2003, which is incorporated by reference, the shape prior of signed distance representations called eigenshapes is extracted by Principal Component Analysis (PCA). When the boundary of an object is unclear and/or noisy, the shape prior is used to obtain plausible delineation.

When searching for lesions in the breast using DCE-MRI, internal structures such as the pectoral muscles that are highly vascularized may light up with the application of the magnetic contrast agent. Thus, the pectoral muscles, and other such structures may make location of breast lesions more difficult. Accordingly, by performing accurate segmentation, vascularized structures that are not associated with the breast tissue may be removed from consideration thereby facilitating fast and accurate detection of breast lesions.

After segmentation has been performed (Step S15), the breast tissue may be isolated and regions of suspicion may be identified within the breast tissue region (Step S16). Identification of the regions of suspicion may be performed either manually by the medical practitioner examining the image data, or automatically by a CAD system. A region of suspicion is a structure that has been determined to exhibit one or more properties that make it more likely to be a breast lesion than the regions of the breast tissue that are not determined to be regions of suspicion.

Manual detection of the region of suspicion may be performed by the medical practitioner in accordance with the many techniques of the field, including examining the medical images for shapes and sizes that may be indicative of a lesion.

Automatic detection of the region of suspicion may be performed by systematically analyzing a neighborhood of voxels around each voxel of the image data to determine whether or not the voxel should be considered part of a region of suspicion. This determination may be made based on the acquired pre-contrast MR image as well as the post-contrast MR image. Such factors as size and shape may be considered.

Moreover, the absorption and washout profile of a given region may be used to determine whether the region is suspicious. This is because malignant tumors tend to show a rapid absorption followed by a rapid washout. This and other absorption and washout profiles can provide significant diagnostic information.

Breast imaging reporting and data systems (BIRADS) is a system that has been designed to classify regions of suspicion that have been manually detected using conventional breast lesion detection techniques such as mammography and breast ultrasound. Under this approach, there are six categories of suspicious regions. Category 0 indicates an incomplete assessment. If there is insufficient data to accurately characterize a region, the region may be assigned to category 0. A classification as category 0 generally implies that further imaging is necessary. Category 1 indicates normal healthy breast tissue. Category 2 indicates benign or negative. In this category, any detected masses such as cysts or fibroadenomas are determined to be benign. Category 3 indicates that a region is probably benign, but additional monitoring is recommended, Category 4 indicates a possible malignancy. In this category, there are suspicious lesions, masses or calcifications and a biopsy is recommended. Category 5 indicates that there are masses with an appearance of cancer and biopsy is necessary to complete the diagnosis. Category 6 is a malignancy that has been confirmed through biopsy.

In particular, when a region of suspicion is characterized as a category 3 region, additional monitoring is generally required. For example, the patient may be instructed to be retested in six months. This category may be particularly problematic because regardless of the outcome, an error has occurred. For example, if a patient is judged to have a category 3 lesion, in six months time that patient will either be found to have no malignancy in which case the patient has been made to endure anguish that could have been avoided, or the patient is found to have a malignancy in which case the malignancy was permitted to go without treatment for six months. In either case, it would have been preferable that the lesion be assigned a different category number.

Figure 3:
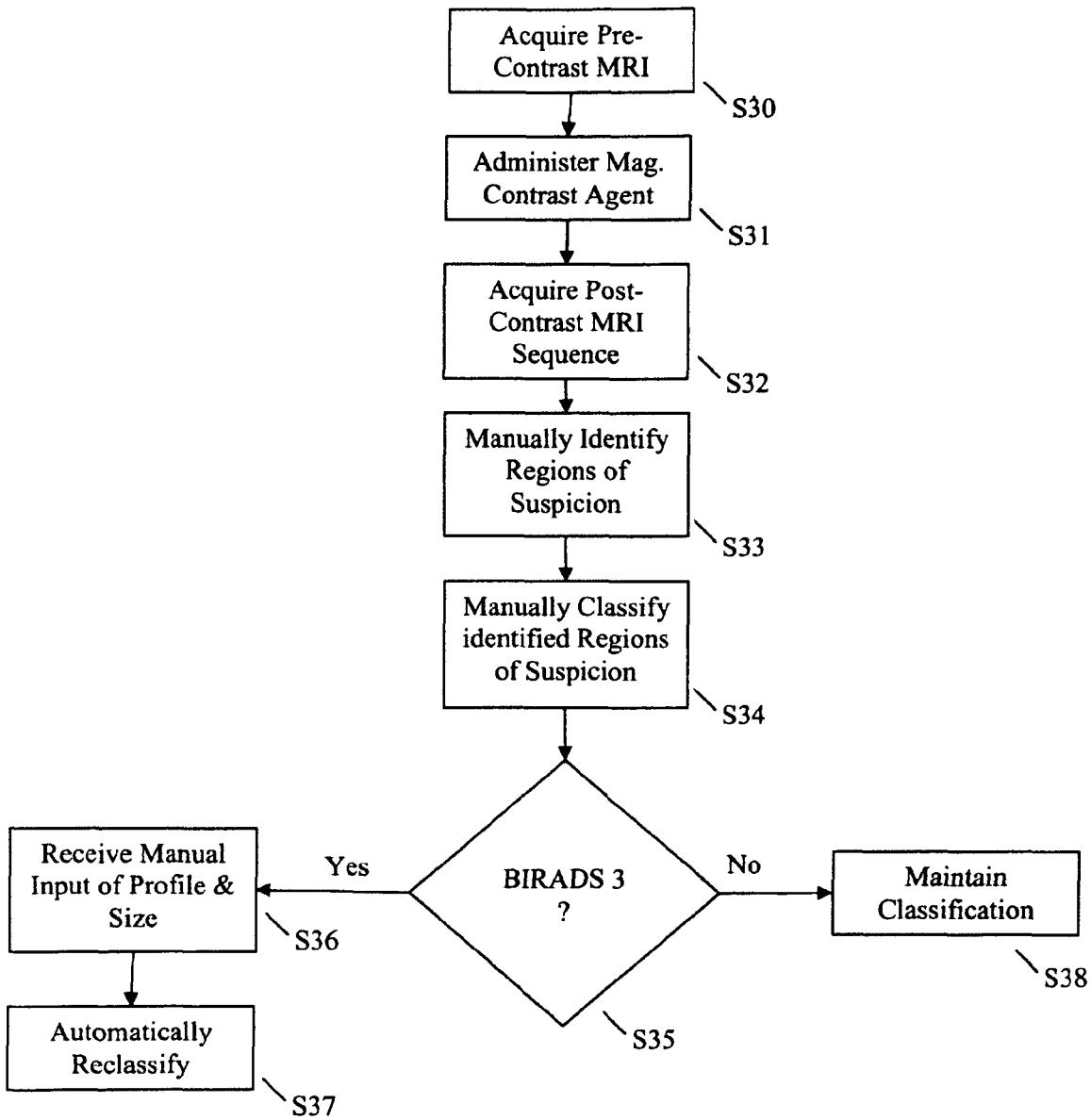
FIG. 3 is a flow chart illustrating a method for imaging a patient's breast using DCE-MRI and rendering a manual diagnosis with the aid of computational analysis according to an exemplary embodiment of the present invention.

Of course, there may always be a region of suspicion that is simply too close to call, however, exemplary embodiments of the present invention seek to minimize category 3 classifications by providing the medical practitioner with a computer-generated assessment as to whether a category 3 classification should be upgraded to a category 4 classification or downgraded to a category 2 classification, in accordance with a novel approach to calculating a probability of malignancy based on manual inputs that is discussed in detail below with respect to FIG. 3

Exemplary embodiments of the present invention may allow for the characterization of a given region according to the above BIRADS classifications based on the DCE-MRI data. To perform this categorization, the absorption and washout profile, as gathered from the post-contrast MRI sequence, for each given region may be compared against a predetermined understanding of absorption and washout profiles.

Figure 2:
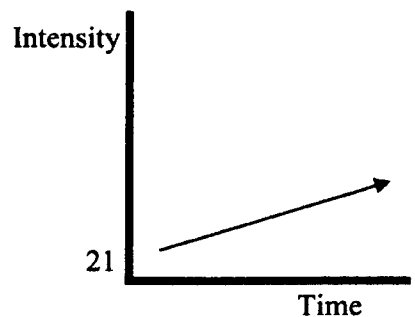
FIG. 2 is a set of graphs illustrating a correspondence between absorption and washout profiles for various BIRADS classifications according to an exemplary embodiment of the present invention.
Figure 2:
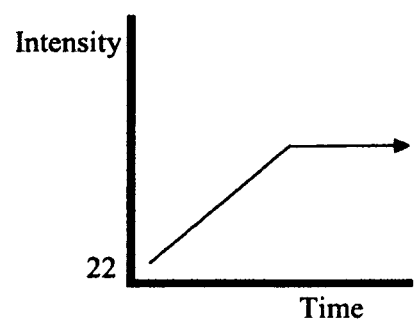
Figure 2:
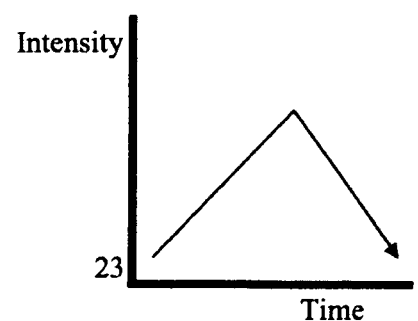

FIG. 2 is a set of graphs illustrating a correspondence between absorption and washout profiles for various BIRADS classifications according to an exemplary embodiment of the present invention. These classifications may be manually provided by the medical practitioner or may be automatically provided by the CAD system.

In the first graph 21, the T1 intensity is shown to increase over time with little to no decrease during the observed period. This behavior may correspond to a gradual or moderate absorption with a slow washout. This may be characteristic of normal breast tissue and accordingly, regions exhibiting this profile may be classified as category 1.

In the next graph 22, the T1 intensity is shown to increase moderately and then substantially plateau. This behavior may correspond to a moderate to rapid absorption followed by a slow washout. This may characterize normal breast tissue or a benign mass and accordingly, regions exhibiting this profile may be classified as category 2.

In the next graph 23, the T1 intensity is shown to increase rapidly and then decrease rapidly. This behavior may correspond to a rapid absorption followed by a rapid washout. While this behavior may not establish a malignancy, it may raise enough suspicion to warrant a biopsy, accordingly, regions exhibiting this profile may be classified as category 3.

The three categories of the absorption/washout need not necessarily coincide with the BIRADS classifications, and indeed, according to exemplary embodiments of the present invention, the medical practitioner may separately determine a BIRADS classification for each suspected lesion and determine an absorption/washout profile category for each suspected lesion. The medical practitioner may of course use the determined absorption/washout profile as part of the diagnosis and BIRADS classification.

Other absorption and washout profiles may be similarly established for other BIRAD categories. In this way, DCE-MRI data may be used to characterize a given region according to the BIRADS classifications. This and potentially other criteria, such as size and shape, may thus be used to identify regions of suspicion (Step S16).

After regions of suspicion have been identified, false positives may be removed (Step S17). This step may be particularly useful when the regions of suspicion were automatically determined by the CAD system, but this step may be omitted when regions of suspicion have been identified manually by the medical practitioner. As described above, artifacts such as motion compensation artifacts, artifacts cause by magnetic field inhomogeneity, and other artifacts, may lead to the inclusion of one or more false positives, especially in the case of automatic determination. Exemplary embodiments of the present invention and/or conventional approaches may be used to reduce the number of regions of suspicion that have been identified due to an artifact, and thus false positives may be removed. Removal of false positives may be performed by systematically reviewing each region of suspicion multiple times, each time for the purposes of removing a particular type of false positive. Each particular type of false positive may be removed using an approach specifically tailored to the characteristics of that form of false positive. Examples of such approaches are discussed in detail below.

After false positives have been removed (Step S17), the remaining regions of suspicion may be further considered by the medical practitioner. In the case where automatic classification has been performed by a CAD system, this step may include presentment of the remaining regions of suspicion to the medical practitioner. For example, the remaining regions of interest may be highlighted within a representation of the medical image data. Quantitative data such as size and shape measurements and/or BIRADS classifications may be presented to the medical practitioner along with the highlighted image data. The presented data may then be used to determine a further course of testing or treatment. For example, the medical practitioner may use the presented data to order a biopsy or refer the patient to an oncologist for treatment.

When identification of regions of suspicion is manually performed by the medical practitioner, the above-described procedure may be simplified in accordance with the approach disused below with respect to FIG. 3.

FIG. 3 is a flow chart illustrating a method for imaging a patient's breast using DCE-MRI and rendering a manual diagnosis with the aid of computational analysis according to an exemplary embodiment of the present invention. As described above with respect to FIG. 1, first, a pre-contrast MRI is acquired (Step S30). The pre-contrast MRI may include an MR image taken of the patient before the magnetic contrast agent has been administered. The pre-contrast MRI may include one or more modalities. For example, both T1 and T2 relaxation modalities may be acquired.

Next, with the patient remaining as still as possible, the magnetic contrast agent may be administered (Step S31). The magnetic contrast agent may be a paramagnetic agent, for example, a gadolinium compound. The agent may be administered orally, intravenously, or by another means. After administration of the magnetic contrast agent, a sequence of post-contrast MR images may be acquired (Step S32). The sequence may be acquired at regular intervals in time, for example, a new image may be acquired every minute.

The medical practitioner may then examine the pre and post contrast medical image data to manually identify one or more regions of suspicion (Step S33). The regions of suspicion may be suspected lesion candidates. After the regions of suspicion have been identified, or while identifying the regions of suspicion, the medical practitioner may manually classify the regions of suspicion (Step S34). Classification of the regions of suspicion may include making a final determination as to whether the region of suspicion is benign or malignant, determining a probability of malignancy, characterizing each region in accordance with BIRADS classifications, and/or characterizing the absorption/washout profile, for example, in accordance with the three categories discussed above with respect to FIG. 2.

After the regions of suspicion have been classified, the computerized system of an exemplary embodiment of the present invention may be used to further classify the regions of suspicion. Use of the computerized system may be optional, for example, it may be utilized when the medical practitioner has determined that one or more identified regions of suspicion is probably benign, but additional monitoring is recommended, a situation that may be classified as BIRADS 3 (Step S35). If it is determined that a region of suspicion is probably benign but more testing is recommended, for example, BIRADS 3, (Yes, Step S35) then the medical practitioner may provide the system with manual input of the absorption/washout profile, for example, by providing one of the three absorption/washout profile categories discussed above with respect to FIG. 2 and an assessment of the size of the region of suspicion (Step S36).

The system may then perform an automatic determination as to the probability of malignancy based on novel techniques discussed in detail below (Step S37). This determination may include an automatic reclassification of the region of suspicion, for example, to upgrade the region of suspicion to BIRADS category 4, downgrade the region of suspicion to BIRADS category 2, or to confirm the BIRADS category 3 classification.

If, however, the medical practitioner determines in Step S35 that the region of suspicion is clearly benign (BIRADS 2 or 1) or that the region of suspicion is clearly malignant (BIRADS 4 and above) (No, Step S35), then the medical practitioner's classification may be maintained (Step S38).

Although exemplary embodiments in which the computerized classification system is only evoked when a region of suspicion has been characterized as BIRADS category 3, other exemplary embodiments of the present invention may evoke the computerized classification system regardless of the assessment of the medical practitioner. In this case, the computerized classification system would provide a probability of malignancy, BIRADS classification or some other form of characterization.

Exemplary embodiments of the present invention may utilize a computerized classification system for receiving region of suspicion parameters such as the characterization of the absorption/washout profile and region of suspicion size and generating the determination as to the probability of malignancy based on these parameters. The parameters may be manually input by a user such as a medical practitioner, and as described above, the probability of malignancy may be expressed as an upgrade, downgrade or confirmation of a BIRADS level 3 classification.

The computerized classification system according to embodiments of the present invention automatically provides this assessment of the probability of malignancy using the above-identified inputs in accordance with the following formula:

$$R_c(s, t) = \frac{2}{\pi}\arctan\left[\left(\frac{st}{c}\right)^3\right] \quad (1)$$

where $R_c$ is the risk of a lesion being malignant, s is the size of the lesion, t is the characterization of the absorption/washout profile, and c is a cutoff size for a progressive lesion to be considered suspicious for malignancy. This cutoff size parameter may be determined using a learning algorithm base on provided training data. The size s may be a diameter of the lesion in units of millimeters. The characterization of the absorption/washout profile may be either 1, 2, or 3, as discussed in detail above with respect to FIG. 2, where classification 1 represented a progressive absorption, classification 2 represented a plateau, and classification 3 represented washout. The cutoff size may be a diameter in millimeters.

The probability $R_c$ may represent a risk factor between 0 and 1, where 0 represents no chance of malignancy and 1 represents a definite malignancy. This probability may be provided to the medical practitioner as an output to aid the medical practitioner in rendering a diagnosis or it may be used to upgrade, downgrade or keep the same an uncertain diagnosis such as BIRADS 3 characterization.

The probability $R_c$ may be used to upgrade, downgrade or maintain a finding of BIRADS 3 by establishing a threshold for which an upgrade or downgrade could occur. According to one exemplary embodiment of the present invention, if the probability $R_c$ is within the range of 0 to ½, then a downgrade to BIRADS 2 is provided while if the probability $R_c$ is within the range of ½ to 1, then an upgrade to BIRADS 4 is provided. Alternatively, there may be some range for which the BIRADS 3 characterization is maintained. For example, a probability $R_c$ within the range of 0 to ⅓ may result in a downgrade, a probability $R_c$ within the range of ⅓ to ⅔ may result in no change, and a probability $R_c$ within the range of ⅔ to 1 may result in an upgrade.

As discussed above, the cutoff size c may be determined using a learning algorithm where multiple instances of training data may be processed. The training data may include a characterization of the lesion size, absorption/washout profile, and whether the lesion turned out to be benign or malignant. The learning algorithm may then use the training data to determine an optimum value for c for which a maximum number of instances of training data are correctly designated as benign or malignant based on the lesion size and the absorption/washout profile.

As an alternative to using a training algorithm to determine an optimum c, a suitable value of c may be predetermined. For example, a value of 23 mm may be used for c. Moreover, a training algorithm may also be used to establish an equation for relating malignancy to lesion size and an absorption/washout profile, rather than using the equation (1) provided above.

Exemplary embodiments of the present invention utilize a relationship between the size of the lesion, the characterization of the absorption/washout profile and the probability of malignancy. This relationship may be as described above with respect to equation (1) or another equation may be used. While equation (1) may be varied with success, exemplary embodiments of the present invention may utilize a relationship where the probability of malignancy is dependent upon a lesion size and absorption/washout profile characterization, each to the power of 3, or more simply:

$$\text{Probability} = (s \cdot t)^3 \quad (2)$$

The resulting probability may then be normalized and/or related to an upgrade/downgrade.

As discussed above, exemplary embodiments of the present invention may provide for a computerized classification system that determines either a probability of malignancy or provides an upgrade/downgrade for a manual diagnosis based on data pertaining to a lesion size and absorption/washout profile that are manually entered by a user such as a medical practitioner. Variations of this basic technique are possible, for example, other factors in addition to or in place of the lesion size and absorption/washout profile may be used to perform the probability determination and/or the data may be automatically acquired rather than manually input. Those of skill in the art would also understand that other modifications would be possible.

In addition to or in place of lesion size and absorption/washout profile information, exemplary embodiments of the present invention may also use one or more of the following other features in determination the probability of malignancy. As is the case with the lesion size and absorption/washout profile information, these other features may be manually entered by the user. These other features may include: an indication of lesion type that may be either a mass or a non-mass; an indication of mass shape, for example, round, oval, lobulated, irregular, etc.; an indication of mass margin, for example, smooth, irregular, spiculated, etc.; an indication of mass enhancement, for example, rim, central, bright septations, dark septations, a combination of bright and dark septations, homogeneous, heterogeneous, etc.; an indication of non-mass distribution, for example, focal area, linear, ductal, segmental, regional, diffuse, etc.; an indication of non-mass internal enhancement, for example, homogeneous, heterogeneous, stippled, clumped, dendritic, reticular, etc. Other examples of features may include indications of lesion location and overall image quality.

Figure 4:
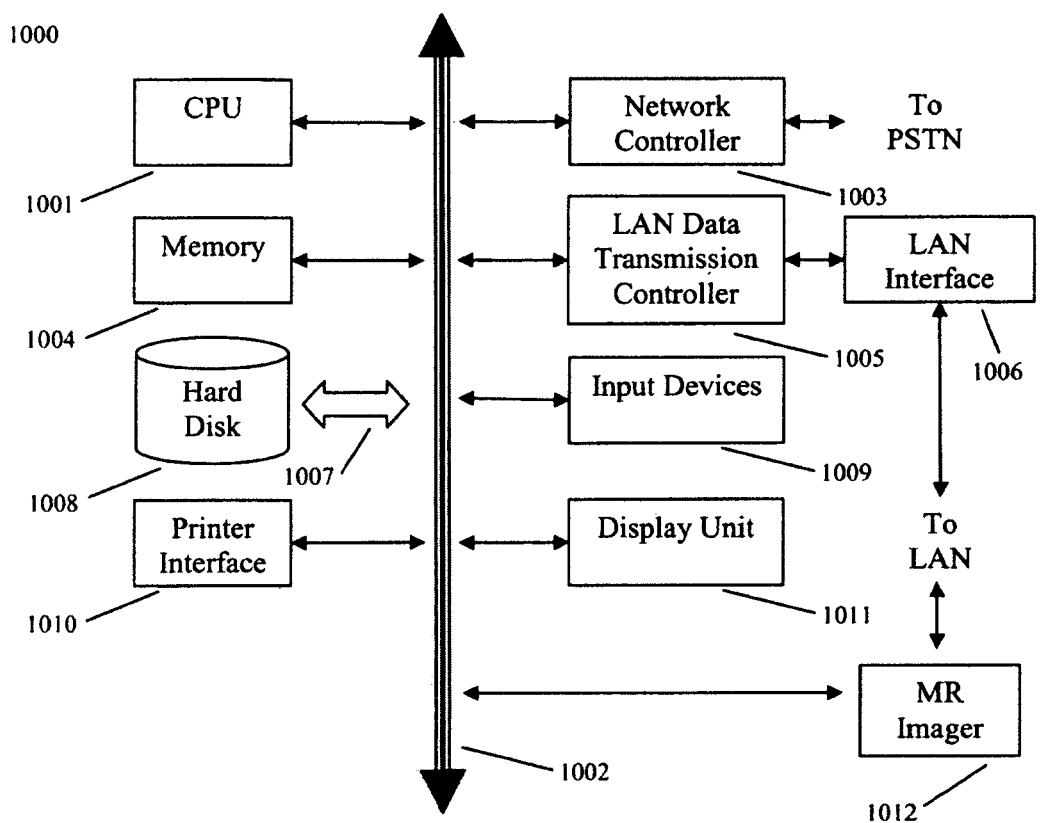
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007. A MR imager 1012 may be connected to the internal bus 1002 via an external bus (not shown) or over a local area network.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for classifying a lesion in an MRI, comprising:
   acquiring, by an MR imager, a pre-contrast MR image;
   administering a magnetic contrast agent;
   acquiring, by the MR imager, a set of post-contrast MR images;
   displaying the acquired pre-contrast and post-contrast MR images;
   receiving, in a computer system, a plurality of manually entered factors pertaining to a lesion manually identified within the pre-contrast and post-contrast MR images, wherein the factors pertaining to the lesion include a manually entered value for a size (s) of a lesion manually identified within the pre-contrast and post-contrast MR images, and a manually entered value for an absorption/washout profile (t) of the manually identified lesion; and
   automatically determining, in the computer system, a risk of malignancy for the manually identified lesion based on the received plurality of factors pertaining to the lesion by normalizing a value of $(s \cdot t)^3$; wherein the absorption/washout profile (t) are expressed as:
   1 when the lesion exhibits a progressive absorption,
   2 when the lesion exhibits a plateau, and
   3 when the lesion exhibits a washout.

2. The method of claim 1, wherein the acquired pre-contrast and post contrast MR images comprise a dynamic contrast enhanced MRI (DCE-MRI).

3. The method of claim 1, wherein the magnetic contrast agent includes a gadolinium compound.

4. The method of claim 1, wherein the value for the size of the lesion and the absorption/washout profile of the lesion are determined by a medical practitioner upon reading the displayed acquired pre-contrast and post-contrast MR images.

5. The method of claim 1, wherein the risk of malignancy $R_c$ is automatically determined from the received size value (s) and absorption/washout profile (t) according to the equation:

$$R_c(s, t) = \frac{2}{\pi} \arctan\left[\left(\frac{st}{c}\right)^3\right]$$

wherein e is a cutoff size for a progressive lesion to be considered suspicious for malignancy.

6. The method of claim 5, wherein c is 23 millimeters.

7. The method of claim 5, wherein c is determined by a training algorithm that uses a set of training data of lesions that includes characterizations of lesion sizes, absorption/washout profiles, and determinations as to whether the lesions turned out to be benign or malignant.

8. A method for classifying a lesion in an MRI, comprising:
   receiving, in a computer system, a manually entered value for a size (s) of a lesion manually identified within DCE-MR images, wherein the lesion has been diagnosed as having an uncertain probability of malignancy;
   receiving, in the computer system, a manually entered value for an absorption/washout profile (t) of the manually identified lesion;
   automatically determining, in the computer system, a risk of malignancy for the manually identified lesion based on the received size value and absorption/washout profile by normalizing a value of $(s \cdot t)^3$; and
   recharacterizing, in the computer system, the diagnosis of the lesion as either being benign or malignant based on the automatically determined risk of malignancy; wherein the absorption/washout profile (t) are expressed as:
   1 when the lesion exhibits a progressive absorption,
   2 when the lesion exhibits a plateau, and
   3 when the lesion exhibits a washout.

9. The method of claim 8, wherein the DCE-MR images were acquired along with the administration of a magnetic contrast agent including a gadolinium compound.

10. The method of claim 8, wherein the value for the size of the lesion and the absorption/washout profile of the lesion are determined by a medical practitioner upon reading the DCE-MR images.

11. The method of claim 8, wherein the risk of malignancy is automatically determined from the received size value (s) and absorption/washout profile (t) according to the equation:

$$R_c(s, t) = \frac{2}{\pi}\arctan\left[\left(\frac{st}{c}\right)^3\right]$$

wherein c is a cutoff size for a progressive lesion to be considered suspicious for malignancy.

12. The method of claim 11, wherein c is 23 millimeters.

13. The method of claim 11, wherein c is determined by a training algorithm that uses a set of training data of lesions that includes characterizations of lesion sizes, absorption/washout profiles, and determinations as to whether the lesions turned out to be benign or malignant.

14. The method of claim 8, wherein the characterization of the lesion as having an uncertain probability of malignancy includes a classification of the lesion as a BIRADS level 3 lesion and the recharacterization of the diagnosis includes either downgrading the lesion to BIRADS level 2, upgrading the lesion to BIRADS level 4 or keeping the lesion as BIRADS level 3.

15. A computer system comprising:
   a processor; and
   a non-transitory program storage device readable by the computer system, tangibly embodying a program of instructions executable by the processor to perform method steps for method for classifying a lesion in an MRI, the method comprising:
      receiving a manually entered value for a size (s) of a lesion manually identified within DCE-MR images, wherein the lesion has been diagnosed as having an uncertain probability of malignancy;
      receiving a manually entered value for an absorption/washout profile (t) of the manually identified lesion;
      automatically determining a risk of malignancy for the manually identified lesion based on the received size value and absorption/washout profile by normalizing a value of $(s \cdot t)^3$; and
      recharacterizing the diagnosis of the lesion as either being benign or malignant based on the automatically determined risk of malignancy; wherein the absorption/washout profile (t) are expressed as:
         1 when the lesion exhibits a progressive absorption,
         2 when the lesion exhibits a plateau, and
         3 when the lesion exhibits a washout.

16. The computer system of claim 15, wherein the risk of malignancy $R_c$ is automatically determined from the received size value (s) and absorption/washout profile (t) according to the equation:

$$R_c(s, t) = \frac{2}{\pi}\arctan\left[\left(\frac{st}{c}\right)^3\right]$$

wherein c is a cutoff size for a progressive lesion to be considered suspicious for malignancy.

17. The computer system of claim 16 wherein c is 23 millimeters.

18. The computer system of claim 16 wherein c is determined by a training algorithm that uses a set of training data of lesions that includes characterizations of lesion sizes, absorption/washout profiles, and determinations as to whether the lesions turned out to be benign or malignant.

* * * * *